United States Patent [19]

Harris

[11] Patent Number: 5,226,896
[45] Date of Patent: Jul. 13, 1993

[54] DOSE INDICATING INJECTION PEN
[75] Inventor: Dale C. Harris, Fairland, Ind.
[73] Assignee: Eli Lilly and Company, Indianapolis, Ind.
[21] Appl. No.: 504,254
[22] Filed: Apr. 4, 1990
[51] Int. Cl.$^5$ .............................................. A61M 5/24
[52] U.S. Cl. ..................... 604/211; 604/208; 604/209; 604/232
[58] Field of Search ............... 604/207–211, 604/218, 224, 246, 232

[56] References Cited

U.S. PATENT DOCUMENTS

| | | | |
|---|---|---|---|
| 3,232,117 | 2/1966 | Gilmont . | |
| 3,613,952 | 10/1971 | Gilmont et al. | 222/43 |
| 3,815,785 | 6/1974 | Gilmont | 222/46 |
| 4,096,751 | 6/1978 | Withers et al. | 73/425.6 |
| 4,367,739 | 1/1983 | LeVeen . | |
| 4,395,921 | 8/1983 | Oppenlander | 73/864.18 |
| 4,413,760 | 11/1983 | Paton | 222/309 |
| 4,475,905 | 10/1984 | Himmelstrup | 604/208 |
| 4,498,904 | 2/1985 | Turner | 604/211 |
| 4,592,745 | 6/1986 | Rex | 604/211 |
| 4,865,591 | 9/1989 | Sams | 604/186 |
| 4,883,472 | 11/1989 | Michel | 604/208 |
| 4,936,833 | 6/1990 | Sams | 604/232 |
| 4,973,318 | 11/1990 | Holm et al. | 604/208 |
| 5,092,842 | 3/1992 | Bechtold et al. | 604/135 |
| 5,112,317 | 5/1992 | Michel | 604/208 |

FOREIGN PATENT DOCUMENTS

| | | |
|---|---|---|
| 87116619.5 | 5/1988 | European Pat. Off. . |
| 89303884.4 | 10/1989 | European Pat. Off. . |
| 89101509.1 | 1/1990 | European Pat. Off. . |
| 1632032 | 12/1967 | Fed. Rep. of Germany . |
| 3031830 | 8/1980 | Fed. Rep. of Germany . |
| WO88/07874 | 10/1988 | PCT Int'l Appl. . |

OTHER PUBLICATIONS

U.S. application Ser. No. 07/361,132 dated Jun. 5, 1989, Harris.

Primary Examiner—C. Fred Rosenbaum
Assistant Examiner—C. Maglione
Attorney, Agent, or Firm—Douglas J. Taylor; Leroy Whitaker

[57] ABSTRACT

Two embodiments of a multi-dose syringe both include structure for indicating the selected amount of liquid to be injected. A first element and a second element coupled respectively to the syringe housing and the plunger rod are adapted for calibrated movement with respect to each other, one of the first and second elements includes an outer portion having dose-indicating scale thereon, and another of the first and second elements surrounding said outer portion includes a window through which only a segment of the dose-indicating scale on said portion is visible, the visible portion indicating the amount of liquid selected for injection.

15 Claims, 2 Drawing Sheets

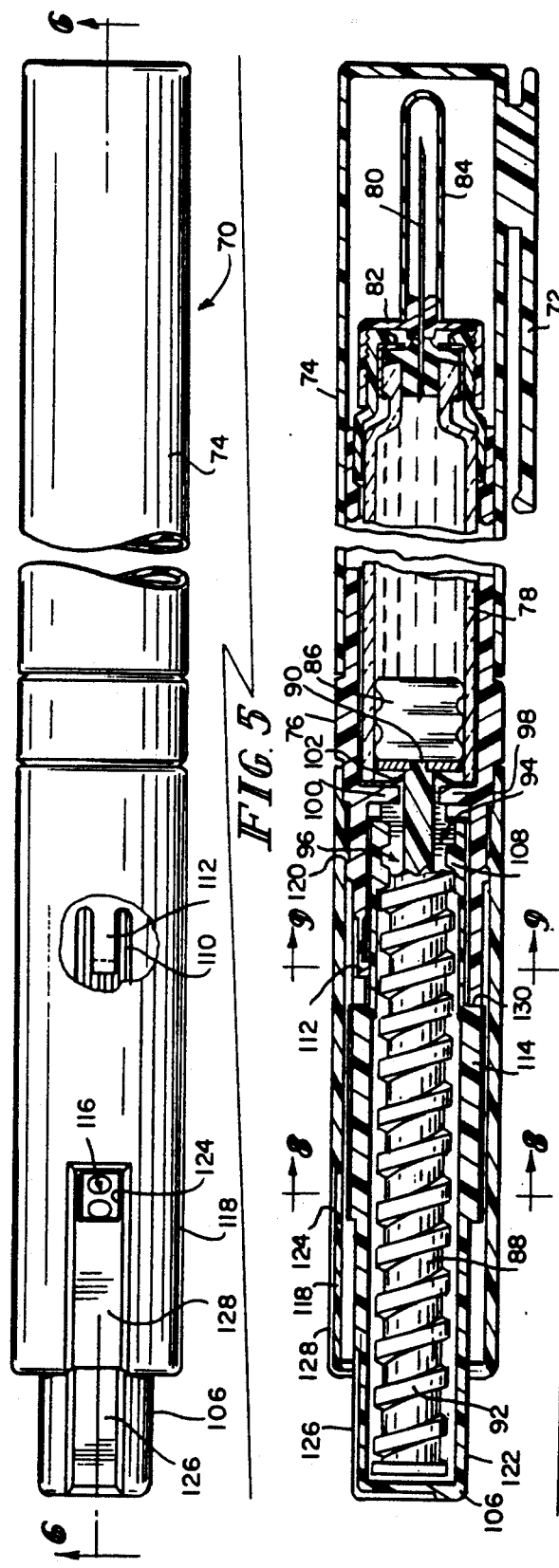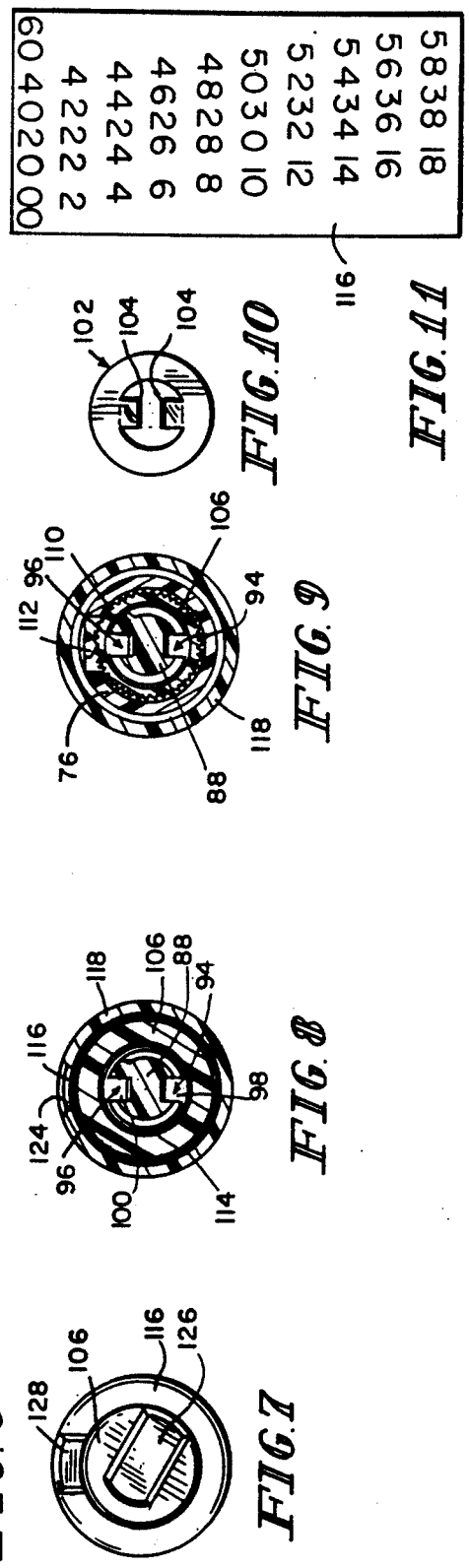

DOSE INDICATING INJECTION PEN

BACKGROUND OF THE INVENTION

The present invention relates generally to devices suitable for use in dispensing a measured amount of liquid material from a container. The invention particularly relates to a hypodermic syringe having the same general appearance as a pen or mechanical pencil which is specifically adapted to provide for multiple measured injections of materials such as insulin or human growth hormone.

Diabetics and others frequently find themselves in situations where the assistance of a health professional is unavailable to administer a subcutaneous or intramuscular injection of measured amount of a liquid agent. In such situations such persons need to have a low cost syringe which does not require the assistance of a health professional to achieve the desired measure of accuracy. It is often the case that such persons require more than one dose per day, each dose being of a somewhat different volume. Dispensers of this general type are known which have the general appearance of a pen or mechanical pencil. The dispenser is typically large enough to hold several such doses, yet it is small enough to fit conveniently in one's pocket or purse. Examples of such devices are to be found in U.S. Pat. Nos. 4,413,760; 4,498,904; and 4,592,745. Additional examples are shown in PCT International Publications WO 87/02895 and WO 88/07874, and in European Patent Application 89101509.1.

In devices of this class, a container of the liquid is generally provided having a closed first end adapted to be penetrated by a needle assembly so as to permit the liquid in the container to pass out the closed first end for subcutaneous or intramuscular injection. The second end of the container is generally closed by a piston. To prevent tampering or reuse of the liquid container, the piston is generally designed such that a pushing force can be applied to the piston to reduce the liquid-holding volume of the container, but no feature is presented which would be suitable for pulling on the piston so as to enlarge the liquid-holding volume of the container.

An elongated member in the nature of a plunger rod is received within the housing for exerting a force on the piston closing the second end of the container. A means is provided for measuring the distance which the plunger rod travels to determine the decrease in volume of the liquid container which causes the dispensing of the liquid within the container. It has generally been recognized that the dispenser should have some feature which would allow the rod to only travel in a single direction toward the piston thereby preventing any action on the part of the rod which might permit an enlargement of the volume of the liquid container. A safety cover is generally provided over a needle assembly attached to the closed end of the container.

While the prior art pen-style syringes have met with some success, certain shortcomings have also been observed. In some prior art pens, the adjustment of the dose to be injected, once made, cannot be accurately diminished to a smaller value. This results in an unnecessary waste of the medicating liquid within the syringe. In some prior art pens, the indication of dose is difficult to read. Prior art pens have generally required the patient to read two scales and/or to do some computations in order to determine the dosage delivered. Further, many prior art devices are specifically intended for repeated use generally by substitution of containers within the syringe which can contribute to the unethical use of the syringe in connection with non-prescribed substances.

SUMMARY OF THE INVENTION

In order to overcome these and other shortcomings of the prior art, a syringe constructed in accordance with the present invention includes a syringe housing, a needle assembly coupled to a distal end of the syringe housing, and a piston movable within the housing to expel liquid from the housing through the needle. A plunger rod having a non-circular cross-section is provided having a distal end in contact with the piston for exerting a force on the piston. An interior surface of the syringe housing includes a non-circular opening corresponding generally to the cross-section of the plunger rod for preventing rotation of the plunger rod with respect to the housing, and means engaging a surface of the plunger rod are provided for preventing movement of the plunger rod away from the needle assembly.

A first element and a second element are coupled respectively to the syringe housing and the plunger rod and are adapted for calibrated movement with respect to each other. One of the first and second elements includes an outer portion having a dose-indicating scale thereon. Another of the first and second elements comprising means surrounding said outer portion including a window through which only some of the dose-indicating scale on said portion is visible, the visible portion completely and unambiguously indicating the amount of liquid selected for injection. Thus, in pens constructed in accordance with the present invention, the patient needs only to read the scale situated in the window to determine the dosage to be delivered. No consideration of multiple scales or computation is required to determine the dosage.

Two specific embodiments illustrative of the present invention are presented. In one embodiment, a collar coupled by threads to the syringe housing is selectively adjustable to vary the desired dosage. Indicia in the form of a dose-indicating scale situated on the collar is hidden by a cap fixed to the plunger rod. A window in the cap permits only a portion of the scale to be viewed, the visible portion being indicative of the dose selected. In this embodiment of the invention, as the liquid is repeatedly dispensed from the syringe, the overall length of the pen diminishes.

In the second illustrated embodiment a collar is rotatably coupled to, but is not longitudinally adjustable with respect to, the syringe housing. A hollow cap coupled by threads to the plunger rod is selectively adjustable to vary the desired dosage. Indicia in the form of a dose-indicating scale situated on the cap is hidden by the collar except for a window in the collar which permits only a portion of the scale to be viewed, the visible portion being indicative of the dose selected. In this embodiment of the invention, the overall length of the pen remains substantially unchanged with repeated use.

In both embodiments, the window can include a lens to enhance the image of the scale. Additionally, both embodiments provide a feature permitting a zeroing of the scale prior to the selected adjustment resulting in the desired dosage. The devices as a whole can be constructed from inexpensive materials and are adapted for machine assembly which contributes directly to a very low manufacturing cost thereby permitting the devices to be disposable. The adjustment of the dose can be increased and decreased thereby diminishing any waste of the medicating liquid. Importantly, the dose indication feature is simply and directly read thereby providing for a more accurate and cost effective use of the medicating liquid dispensed from the apparatus.

Additional features and advantages will become apparent to those skilled in the art from the following detailed discussion of preferred embodiments exemplifying the best mode of carrying out the invention as presently perceived. The detailed description particularly refers to the accompanying drawings.

BRIEF DESCRIPTION OF THE DRAWINGS

FIG. 5 is an front elevation view of a second embodiment of the present invention partially broken away.

FIG. 6 is a sectional detail view taken along lines 6—6 of FIG. 5.

FIG. 7 is a view of the left end of the embodiment shown in FIG. 5 with the collar rotated with respect to the cap.

FIG. 8 is a sectional view taken through line 8—8 of FIG. 6.

FIG. 9 is a sectional view taken through line 9—9 of FIG. 6.

FIG. 10 is a plan view from the right side of FIG. 6 of the push-washer.

FIG. 11 is a plan view of the dose-indicating scale used in connection with the second embodiment of the invention.

DESCRIPTION OF THE PREFERRED EMBODIMENTS

Figure 1:
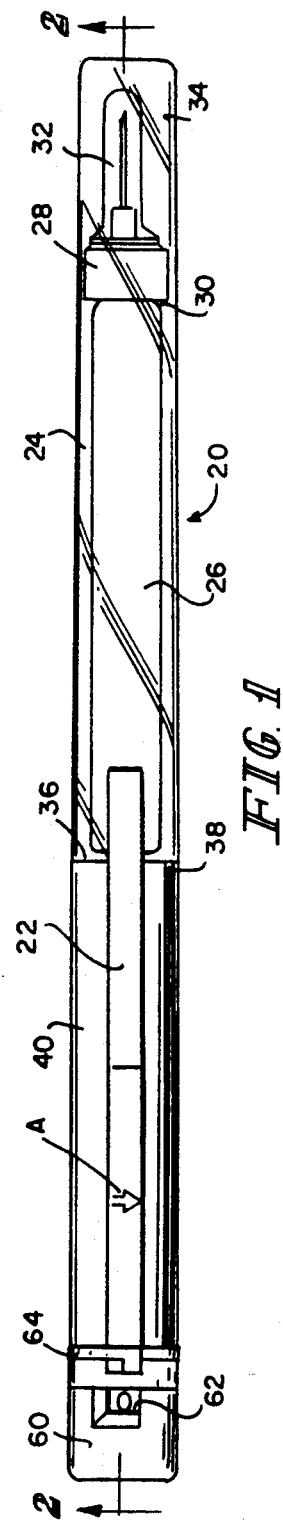
FIG. 1 is a front elevation view of a first embodiment of the invention.

A syringe 20 is shown in FIG. 1 to be constructed to include a pocket clip 22 and to otherwise have the general appearance of a pen or mechanical pencil. The syringe 20 includes a syringe housing 24 which holds within it a container 26 containing a liquid. A needle assembly 28 is coupled to a distal end 30 of the housing 24 and includes a removable protective cover 32. An overcap 34, shown to be transparent in FIG. 1, is provided which envelops the syringe housing 24, needle assembly 28, and protective cover 32.

Figure 2:
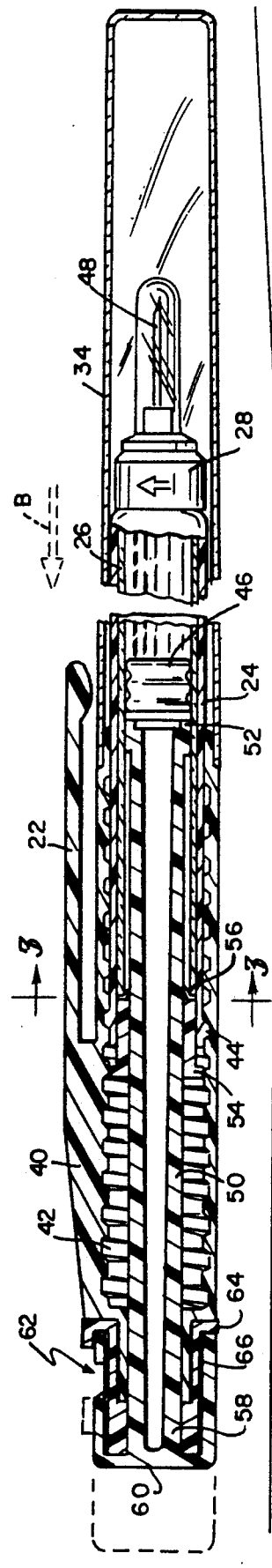
FIG. 2 is an enlarged sectional detail taken along line 2—2 of FIG. 1 partially broken away.

The proximal end 36 of overcap 34 is coupled to the distal end 38 of collar 40. Collar 40 is shown in FIG. 2 to be unitary with clip 22. The collar 40 includes an interior threaded surface 42 which engages the proximal end 44 of syringe housing 24 thereby permitting relative movement between the syringe housing 24 and the collar 40. A piston 46 is situated within the container 26 so as to expel the contained liquid through the needle 48.

Figure 3:
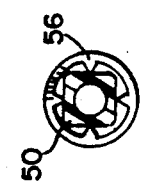
FIG. 3 is a dead sectional view taken through line 3—3 of FIG. 2.

A plunger rod 50 includes a distal end 52 which contacts the piston 46 for exerting a liquid dispensing force on the piston. The plunger rod 50 is shown in FIG. 3 in cross section to have a non-round exterior configuration. A retainer 54 is fixed within the syringe housing 24 at a fixed rotational position and includes an interior surface having a configuration matching the exterior surface of plunger rod 50 to prevent relative rotation between the plunger rod 50 and the syringe housing 24. A push-washer 56 is sandwiched between retainer 54 and container 26 and engages the surface of plunger rod as shown in FIG. 3 to prevent movement of the plunger rod 50 away from the needle assembly 28. This ensures that the only motion available for the plunger rod 50 is one which will cause liquid to be dispensed from the container 26.

Figure 4:
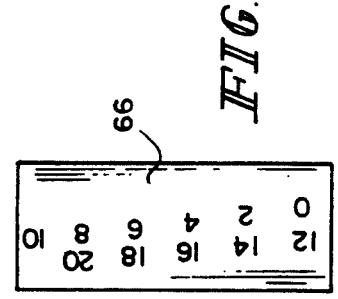
FIG. 4 is a plan view of the dose-indicating scale used in the first embodiment.

The proximal end 58 of plunger rod 50 includes an integral cap 60. The cap includes a window 62. The window 62 overlies element 64 which carries on an outer surface a pattern of indicia forming a dose-indicating scale 66 as shown in FIG. 4. The element 64 is frictionally engaged to collar 40 and generally moves with collar 40 relative to cap 60.

In operation, the syringe 20 initially appears as shown in FIG. 1. To dispense a desired amount of liquid from the syringe 20, the overcap 34 is removed from the syringe telescopically to the right of FIG. 1. The collar 40 is then rotated in the direction of arrow A thereby causing displacement of the collar 40 axially toward the right. As this rotational and axial displacement of collar 40 occurs with respect to the syringe housing 24, through the interaction of the interior threaded surface 42 and the syringe housing proximal end 44, the cap 60 is effectively displaced both rotationally and axially in the direction of arrow B toward the position shown in phantom at the extreme left of FIG. 2.

As this displacement occurs, the segment of the dose-indicating scale 66 which is visible through window 62 varies thereby showing a linear increase in the numbers illustrated in FIG. 4 to indicate an increasing dosage of liquid to be dispensed. The desired dosage can thereby be selected by viewing the dose-indicating scale through the window 62. It is to be noted that the collar 40 is free to rotate in either direction thereby permitting both upward and downward adjustment of the dosage should the desired dosage be inadvertently be passed during the act of adjustment.

Once the desired dosage is selected, the protective cover 32 is removed from the needle assembly 28 and the needle 48 is situated for appropriate subcutaneous or intramusculear injection of the liquid contained within container 26. Once the needle 48 is appropriately positioned, a force is applied to the end of cap 60 causing a linear displacement of the cap, integral plunger rod 50, and piston 46 toward the right to dispense the liquid from the container 26. The dispensing displacement of the plunger rod 50 is halted by the abutting contact between cap 60 and element 64.

Once the desired amount of liquid has been dispensed from the syringe 20, the needle 48 is removed from the injection position and the protective cap 32 replaced. The overcap 34 is also then replaced. Finally, element 64 can be forcibly rotated with respect to collar 40 until the scale "0" appears in the window 62. It is to be noted that with each successive use of a syringe 20, the syringe housing 24 retreats further within the collar 40 which gives the user of such a dispensing pen a rough visual indication of the amount of liquid remaining in the syringe.

In a second preferred embodiment, a syringe 70 according to the present invention shown in FIG. 5 et seq. includes a pocket clip 72 and otherwise has the general appearance of a pen or mechanical pencil. In syringe 70, the pocket clip 72 is formed as part of overcap 74 which is slidably received over syringe housing 76. The syringe housing 76 includes a container 78 of liquid to be dispensed through needle 80 of needle assembly 82, the needle assembly including a protective cover 84 similar to that of syringe 20. The container 78 includes a piston 86 which when displaced to the right of FIG. 6 causes the liquid within the container 78 to be expelled through the needle 80.

A plunger rod 88 includes a distal end 90 contacting piston 86. The plunger rod 88 includes a spiral outer surface 92 interrupted by a pair of longitudinal channels 94 and 96 which are best illustrated in FIGS. 8 and 9. The syringe housing 76 includes a pair of inwardly projecting fingers 98 and 100 engaged in slots or channels 94 and 96 to prevent rotation of the plunger rod 88 with respect to the syringe housing 76. A push-nut 102, as shown in FIG. 10, is sandwiched between the distal surfaces of fingers 98 and 100 and the proximal end of container 78. The inwardly projecting prongs 104 on the push-nut 102 project into slots or channels 94 and 96 to engage the base of each channel preventing movement of the plunger rod 88 away from the needle assembly 82.

A hollow cap 106 envelops the plunger rod 88 and is engaged with the spiral surface 92 of the plunger rod 88 by an inwardly threaded portion 108 near the distal end of the cap 106. The cap 106 includes an externally serrated portion 110 which interacts with a projecting finger 112 of syringe housing 76 to create a sensible vibration in the event of rotation of the cap 106 relative to the syringe housing 76. Alternatively, cap 106 can include a flexible member projecting outward from said cap which engages a grooved interior surface of syringe housing 76 so as to create a sensible vibration in the event of rotation of cap 106 relative to syringe housing 76. An outer portion of the cap 114 carries indicia forming a dose-indicating scale 116 as shown in FIG. 11.

A collar 118 is mounted to the syringe housing 76 by detent 120 and is rotatable with respect to the housing 76. The collar envelops all but a projecting portion 122 of cap 106. A window 124 in collar 118 permits visual inspection of a limited portion of the scale 116 carried by the outer portion 114 of cap 106. Both cap 106 and collar 118 include a surface feature 126 and 128, respectively, for zeroing the collar 118 with respect to the cap 106.

In operation, one seeking to use syringe 70 to inject a selected amount of liquid first rotates collar 118 with respect to syringe housing 76 to a position where a double-zero scale is visible through window 124 as shown in FIG. 5. The collar and cap are designed so that this zeroing of scale 116 is automatically achieved by rotating collar 118 with respect to syringe housing 76 until the surface features 126 and 128 are aligned as shown in FIG. 5.

The projecting portion 122 of cap 106 is then rotated with respect to the syringe housing 76. This rotation of the cap 106 causes the cap to ride up the threads 92 of plunger rod 88 thereby moving axially to the left as shown in FIGS. 5 and 6. The rotation also causes the portion of scale 116 visible through window 124 to be modified with the scale numbers increasing as in the first embodiment. The rotation of cap 106 with respect to syringe housing 76 also causes finger 112 to ride over the grooves of the serrated surface 110 causing a sensible movement of the finger 112. By dimensioning the grooves appropriately, the number of grooves traversed by finger 112 can match the scale visible through window 124. The sensible movement of the flexible finger 112 coupled with the initial zeroing achieved by the co-alignment of surface features 126 and 128 permits use of the syringe 70 by a visually impaired person.

At such time as the scale for the desired dosage is achieved in window 124, the overcap 74 can be removed from the syringe 70. The protective cover 84 can also be removed from the needle 80 and the needle appropriately placed for injection. Pressure is then applied to the end of cap 106 causing it to move axially with the plunger rod 88 toward the needle assembly 82. The movement of the plunger rod forces piston 86 to expel liquid from the liquid container 78 through the needle 80. Movement of the cap 106 and plunger rod 88 is terminated by the abutment between the cap 106 and syringe housing 76 at stop 130. During such axial movement of cap 106, the projecting finger 112 slides within a single groove 110 thereby restricting the cap 106 from any rotational movement relative to the syringe housing 76 which would cause a modification of the selected dosage.

After the selected dosage has been injected, the needle 80 is removed from its injection position and the protective cover 84 repositioned as shown in FIG. 6. The overcap can then also be replaced. Except when the amount selected for injection was 20, 40, or 60 scale units, the relative position between cap 106 and collar 118 will be other than an aligned position and will thus appear something like that shown in FIG. 7. The collar 118 can now be rotated relative to the syringe housing 76 to the zero position as previously described so that the syringe 70 is ready for a subsequent selection of a measured amount of liquid.

Figure 12:
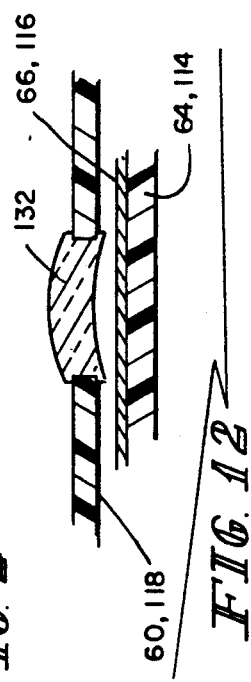
FIG. 12 is a sectional view of a lens incorporated into a window of either embodiment of the invention.

FIG. 12 shows in cross section a window from either embodiment which includes a lens 132 which acts to enlarge the image of the dose-indicating scale. While only the second illustrated embodiment includes a flexible member 112 adapted for a sensible movement during the calibrated adjustment of the syringe, such a feature could be included in syringe 20. Although the invention has been described in detail with reference to the two illustrated preferred embodiments, other variations and modifications exist within the scope and spirit of the invention as described and as defined in the following claims.

What is claimed is:

1. A syringe for containing a liquid to be injected including means for selectively adjusting the amount of liquid to be injected and means for indicating the amount selected comprising:

a syringe housing having a proximal and a distal end, a piston movable within the housing to expel the liquid, and a plunger rod having a first end in contact with the piston for exerting a force on the piston;

a first element and a second element coupled respectively to the syringe housing and the plunger rod and adapted for calibrated movement with respect to each other, one of the first and second elements including an outer portion having a dose-indicating scale thereon, and another of the first and second elements comprising means surrounding said outer portion including a window through which only a segment of the dose-indicating scale on said portion is visible, the visible segment indicating the amount of liquid selected for injection.

2. A syringe according to claim 1 further comprising rotation preventing means within the syringe housing for preventing rotation of the plunger rod with respect to the syringe housing.

3. A syringe according to claim 2 wherein the rotation preventing means comprises an interior surface of the syringe housing having a non-cylindrical opening corresponding generally to a cross-section of the plunger rod for preventing rotation of the plunger rod with respect to the housing.

4. The improvement of claim 2 further comprising rotation preventing means within the syringe housing for preventing rotation of the plunger rod with respect to the syringe housing, the rotation preventing means including prevention means engaging a surface of the plunger rod for preventing movement of the plunger rod away from a distal end of the syringe housing.

5. A syringe according to claim 1 further comprising a needle assembly coupled to a distal end of the syringe housing; and prevention means engaging a surface of the plunger rod for preventing movement of the plunger rod away from the needle assembly.

6. A syringe according to claim 5 further comprising a stop means surrounding the plunger rod for stopping movement of the second element toward the needle assembly upon injection of the selected amount of liquid.

7. The improvement of claim 5 further comprising a container of liquid having a proximal and a distal end situated within the syringe housing, said prevention means contacting a proximal end of the container of liquid for maintaining the container in fixed position with respect to the syringe housing.

8. A syringe according to claim 1 wherein the first element comprises a collar including means for movably engaging the collar to the syringe housing, and wherein the window further comprises a lens for enlarging the appearance of the visible portion of the dose-indicating scale.

9. A syringe according to claim 8 wherein the second element comprises a cap coupled to the plunger rod, the cap including said dose-indicating scale on an outer portion thereof, only a segment of the dose-indicating scale being visible through said window and lens in said collar.

10. A syringe for containing a liquid to be injected including means for selectively adjusting the amount of liquid to be injected and means for indicating the amount selected comprising:
a syringe housing, a piston movable within the syringe housing to expel the liquid, and a plunger rod having a first end in contact with the piston for exerting a force on the piston;
a hollow cap enveloping a second end of the plunger rod end opposite the first end including means for calibrated adjustment of the cap relative to the plunger, an outer portion of the cap having a dose-indicating scale thereon for indicating calibrated movement of the cap with respect to the plunger rod; and
a collar surrounding a distal end of the hollow cap and adapter for calibrated movement with respect thereto, rotatably coupled to the syringe housing, the collar including a window through which only a segment of the dose-indicating scale on said portion of the cap is visible, the visible portion indicating the amount of liquid selected for injection.

11. A syringe according to claim 10 wherein the hollow cap further comprises a flexible member projecting outward from the cap and the syringe housing further comprises a grooved interior surface, said flexible member engaging said grooved interior surface of the syringe housing, such that the calibrated adjustment of the cap causes sensible movement of the flexible member.

12. A syringe according to claim 10 wherein the hollow cap and collar both include a common surface feature to permit zeroing of the collar with respect to the cap by a visually impaired person prior to said calibrated adjustment of the cap with respect to the plunger rod.

13. A syringe according to claim 10 further comprising a lens situated in the window for enlarging the appearance of the visible portion of the dose-indicating scale.

14. A syringe according to claim 10 wherein the hollow cap further comprises an externally grooved surface and the syringe housing further comprises a flexible member projecting outward from the syringe housing into engagement with said grooved surface of the cap, such that the calibrated adjustment of the cap causes sensible movement of the flexible member.

15. A syringe for containing a liquid to be injected including means for selectively adjusting the amount of liquid to be injected and means for indicating the amount selected comprising:
a syringe housing, a needle assembly coupled to a distal end of the syringe housing, a piston movable within the housing to expel liquid from the housing through the needle, a plunger rod having a non-circular cross-section and a distal end in contact with the piston for exerting a force on the piston, an interior surface of the syringe housing having a non-circular opening corresponding generally to the cross-section of the plunger rod for preventing rotation of the plunger rod with respect to the housing, and means engaging a surface of the plunger rod for preventing movement of the plunger rod away from the needle assembly;
a first element and a second element coupled respectively to the syringe housing and the plunger rod and adapted for calibrated movement with respect to each other, one of the first and second elements including an outer portion having dose-indicating scale thereon, and another of the first and second elements comprising means surrounding said outer portion including a window through which only a segment of the dose-indicating scale on said portion is visible, the visible portion indicating the amount of liquid selected for injection.

* * * * *

UNITED STATES PATENT AND TRADEMARK OFFICE
CERTIFICATE OF CORRECTION

PATENT NO.    : 5,226,896

DATED         : July 13, 1993

INVENTOR(S)   : Dale C. Harris

It is certified that an error appears in the above-identified patent and that said Letters Patent is hereby corrected as shown below:

Column 8, Line 1, delete "collar", and insert therefor --collar,--

Column 8, Line 2, delete "adapter", and insert therefor --adapted--

Signed and Sealed this

Twenty-seventh Day of September, 1994

Attest:

BRUCE LEHMAN

Attesting Officer    Commissioner of Patents and Trademarks